United States Patent [19]

Choi

[11] Patent Number: 4,657,531
[45] Date of Patent: Apr. 14, 1987

[54] THERAPEUTIC HEATING APPARATUS

[76] Inventor: Jei C. Choi, 491, Seocho-Dong, Kangnam-ku, Seoul, Rep. of Korea

[21] Appl. No.: 810,580

[22] Filed: Dec. 19, 1985

[30] Foreign Application Priority Data

Feb. 10, 1985 [KR] Rep. of Korea .............. 12843/1985

[51] Int. Cl.⁴ .......................................... A61M 37/00
[52] U.S. Cl. ..................................... 604/23; 128/399; 604/291
[58] Field of Search ...................... 126/204; 128/303.1, 128/399, 400; 604/291, 113, 114, 19, 23, 24

[56] References Cited

U.S. PATENT DOCUMENTS 1,831,669 11/1931 Kono ........................................ 604/24
2,787,998 4/1957 Grossi et al. ........................ 604/291
4,090,517 5/1978 Takenaka ........................ 128/303.1

Primary Examiner—C. Fred Rosenbaum
Assistant Examiner—J. L. Kruter
Attorney, Agent, or Firm—Birch, Stewart, Kolasch & Birch

[57] ABSTRACT

A therapeutic heating apparatus for use in treating portions of the human body which comprises an electrical heater, a heat-conducting plate, a cotton pad and a cotton cover. The pad contains mugwart extracts and/or medicinal ingredients.

7 Claims, 5 Drawing Figures

THERAPEUTIC HEATING APPARATUS

BACKGROUND AND FIELD OF THE INVENTION

The present invention relates to a therapeutic heating apparatus and more particularly to an electric heating cup which comprises a cotton pad containing extracts of mugwort herb or other pharmaceutical ingredients and a heating member for vaporizing the ingredients in the pad. The therapeutic heating appliance is utilized by the patient for treating various portions of the body. Thus, the vapor produced from the medical ingredients of the pad penetrate the body of the patient due to heating energy and pressure.

Many types of therapeutic heating devices are well known in the art. It is also known to treat portions of the body by placing a dry mugwort pill on the relevant portion and burning the pill. However, this treatment can result in burning the human body. Known fumigators which are used to burn mugwort do not control the temperature of the contacting surfaces. Also, it is difficult to treat the sloped portions of the body by using conventional thereapeutic heating devices.

OBJECTS AND SUMMARY OF THE INVENTION

It is therefor an object of the present invention to provide a therapeutic heating apparatus which does not produce hurb ash or smoking gas.

Another object of the present invention is to provide a heating apparatus which houses a pad containing mugwort herb tonics or medicinal ingredients which are vaporized by heating to treat various portions of the human body.

Other objects and further scope of applicability of the present invention will become apparent from the detailed prescription given hereinafter. It should be understood, however, that the detailed description while indicating preferred embodiments of the invention, are given by way of illustration only, since various changes and modifications within the spirit and scope of the invention will become apparent to those skilled in the art from this detailed description.

Briefly, the present invention relates to a therapeutic heating apparatus comprising a base member having a handle, an electric heater, a detachable or attachable heat conducting plate, a dry pad containing mugwort hurb tonics or active ingredients, and a cotton cover to cover the pad for portions of the human body. Thus, the vapor produced from the medicinal ingredients of the pad by heat penetrate into the body of the patient with heating energy and pressure for treating and healing up the human body.

BRIEF DESCRIPTION OF THE DRAWINGS

The present invention will become more fully understood from the detailed prescription given hereinbelow and the accompanying drawings which are given by way of illustration only, and thus are not limitative of the present invention, and wherein.

DETAILED DESCRIPTION OF THE INVENTION

Figure 1:
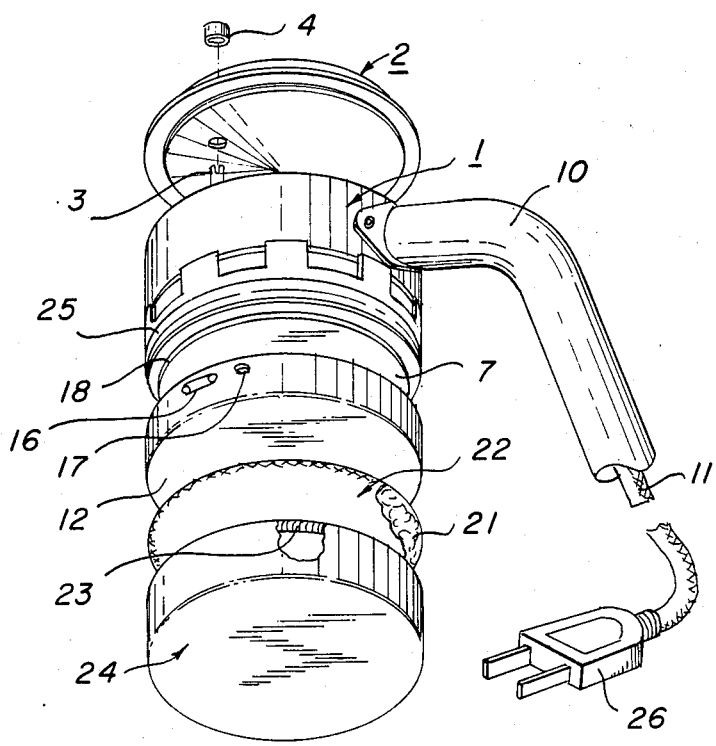
FIG. 1 is an exploded view showing the basic components of the heating apparatus according to the present invention.
Figure 3:
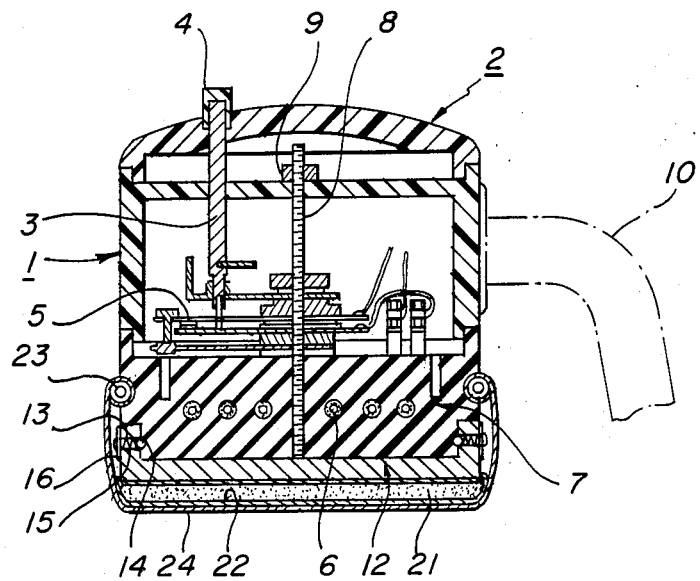
FIG. 3 is a sectional view of the heating a apparatus showing a preferred embodiment of the therapeutic heating device according to the present invention.

Referring now in detail to the drawings for the purpose of illustrating the present invention, the therapeutic heating apparatus as shown in FIG. 1 comprises a base member 1 containing a handle 10, a cover 2 for covering the base member, an electrical heater 7 attached to the base by a bolt 8 and a nut 9 (see FIG. 3), a heat conducting plate 12 attached to the heater 7, a dry cotton pad 22 adapted to contain mugwort hurb (*Artemisian vulgaris*) tonic and/or other medicinal ingredients 21 and a cotton cover 24 which covers the conducting plate 12 and the cotton pad 22. The base member 1 contains a thermostat 5 which connects with the vertical element 4 which passes through the upper portion of the base member 1 and extends through the cover 2 as shown in FIG. 3. A temperature control nub 4 is utilized to set the thermostat 5 as well as to close the cover 2 on the base member 1. The electrical heater includes a series of heating wires 6 which connect to a cord 11 which extends through a handle 10. The cord 11 contains a plug 26. The handle 10 is made of an elastic material such as a soft plastic so that it can be slidably turned to several directions. Also, the length of the handle 10 can be adjusted for easy handling.

Figure 2:
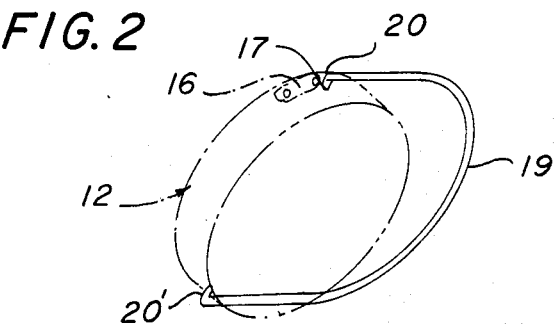
FIG. 2 is a perspective view of the heat conducting plate containing a semicircular elastic ring.

The heat conducting plate 12 can be formed as a concave surface A (FIG. 4) or a convex surface B (FIG. 5) to accommodate the curvatures of the affected portions of the human body. FIG. 2 shows the heat conducting plate 12 which includes apertures 17 symmetrically disposed for engaging a semicircular elastic ring 19 containing curvatures 20, 20' at both ends thereof, whereby the user can separate the plate 12 from the heater 7. The conducting plate 12 is separated from the heater 7 by merely pulling out the elastic ring 19 which disposes the heat conducting plate 12 from the heater 7. Also, balls 14 are provided with springs 15 and extend through holes 13 disposed in the walls of the conducting plate 12 for spring based engagement with grooves 18 disposed in the lower portion of the heater 7. A small plate 16 facilitates the attachment of the spring 15 to the conducting plate on both sides. The pad 22 contains a plurality of cotton pills containing mugwort hurb tonic or medicinal ingredients absorbed therein and in a completely dried state. The cotton cover 24 for covering the conducting plate and the pad, has a coil spring 23 disposed at its circumferential end whereby the coil spring can attach to a ring groove 25 provided in the heater.

Figure 4:
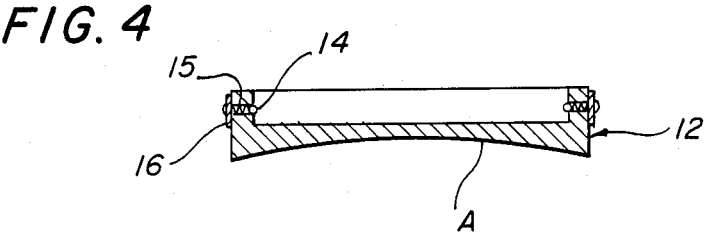
FIG. 4 is a sectional view of the heat conducting plate with a concave configuration according to the present invention.
Figure 5:
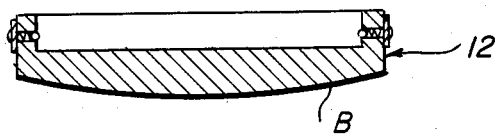
FIG. 5 is a sectional view of the heat conducting plate with a convex configuration according to the present invention.

When it is desired to treat an affected portion of the human body, the user should first select the most appropriate heat conducting plate. For example, for the legs or arms, it is better for the user to select a plate formed with a concave surface as shown in FIG. 4 and ultimately, for the breast, it may be desirable to select a convex surface as shown in FIG. 5. Also, the user can select the medicinal ingredients according to the kind of disease. To assemble the device the heater is connected to the base member. The heat conducting plate is attached to the heater and the pad and cotton cover are attached to the heater by the ring spring 23. Prior to assembly, the pad is pre-wetted. When the plug 26 is connected to a power source, the pre-wetted pad is heated by the electric heater and the heat conducting plate. The vapor evaporating from the pad can then be used to penetrate any desired portion of the human body. The heat energy and pressure simultaneously act to treat the effected portion. Also, the temperature can be controlled by using the thermostat nub 4 on the cover 2. The cotton cover 24 fully covers the pad and the heat conducting plate so that the user cannot be burned by the device. The apparatus of the present invention cannot adversely effect the environment since there is no burning system.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A therapeutic heating apparatus for the human body comprising
   a base member,
   a cotton pad member,
   a heater assembled with the base member,
   a heat conducting plate assembled with the heater, said heat conducting plate containing spring-biased ball means for attachment to the heater,
   said cotton pad member contains a plurality of cotton pills impregnated with mugwort herb or other medicinal ingredient absorbed therein, and
   a cotton cover disposed to cover the cotton member and the heat conducting plate whereby upon the heating of the heater, the medicinal ingredients are evaporated to penetrate any desired portion of the body.

2. The therapeutic heating apparatus of claim 1 wherein the base member includes a thermostat connected to the electrical heater for controlling the heating temperature.

3. The therapeutic heating apparatus of claim 1 wherein the base member is provided with a handle which houses an electric cord.

4. The therapeutic heating apparatus of claim 1 wherein the heat conducting plate includes apertures symmetrically for attaching corresponding curvatures disposed symmetrically at ends of a semicircular elastic ring thereto.

5. The therapeutic heating apparatus of claim 1 wherein the heater contains a groove for receiving the spring based balls and the cover contains a ring spring disposed at the periphery thereof for covering the pad and the heat conducting plate.

6. The therapeutic heating apparatus of claim 1 wherein the heat conducting plate is covered.

7. The therapeutic heating apparatus of claim 1 wherein the heat conducting plate is concave.

* * * * *

UNITED STATES PATENT AND TRADEMARK OFFICE
CERTIFICATE OF CORRECTION

PATENT NO. : 4,657,531
DATED : April 14, 1987
INVENTOR(S) : Jei C. CHOI

It is certified that error appears in the above-identified patent and that said Letters Patent is hereby corrected as shown below:

On the Title Page:

In category " {30} Foreign Application Priority Data ", please change "Feb. 10, 1985" to --October 2, 1985--.

Signed and Sealed this

Seventeenth Day of May, 1988

Attest:

DONALD J. QUIGG

*Attesting Officer*    *Commissioner of Patents and Trademarks*